(12) United States Patent
Reyes (10) Patent No.: US 10,780,243 B2
(45) Date of Patent: Sep. 22, 2020

(54) METHOD AND APPARATUS FOR TREATMENT OF HUMAN URINARY INCONTINENCE

(71) Applicant: Javier G. Reyes, San Antonio, TX (US)

(72) Inventor: Javier G. Reyes, San Antonio, TX (US)

(*) Notice: Subject to any disclaimer, the term of this patent is extended or adjusted under 35 U.S.C. 154(b) by 297 days.

(21) Appl. No.: 14/162,556

(22) Filed: Jan. 23, 2014

(65) Prior Publication Data
US 2014/0214009 A1 Jul. 31, 2014

Related U.S. Application Data

(60) Provisional application No. 61/756,725, filed on Jan. 25, 2013.

(51) Int. Cl.
*A61M 25/00* (2006.01)
*A61F 2/04* (2013.01)

(52) U.S. Cl.
CPC .............................. *A61M 25/0017* (2013.01)

(58) Field of Classification Search
CPC .......... A61M 25/0075; A61M 25/0017; A61M 25/00; A61M 2210/1082; A61M 2210/1085; A61M 2210/1089; A61M 2210/1092; A61M 2210/1096; A61M 25/10; A61M 25/1009; A61M 2025/1093; A61M 25/1002; A61M 2025/1047; A61M 2025/0293; A61M 25/04; A61M 27/002; A61F 9/00781; A61F 2009/00891
See application file for complete search history.

(56) References Cited

U.S. PATENT DOCUMENTS

| | | | |
|---|---|---|---|
| 2,969,066 A | 1/1961 | Holter et al. | |
| 3,332,371 A | 7/1967 | Rochhi et al. | |
| 3,811,448 A * | 5/1974 | Morton | A61M 25/1002 604/102.02 |
| 3,812,841 A | 5/1974 | Isaacson | |
| 4,432,757 A | 2/1984 | Davis, Jr. | |
| 4,932,938 A | 6/1990 | Goldberg et al. | |
| 4,968,294 A | 11/1990 | Salama | |
| 5,041,092 A | 8/1991 | Barwick | |
| 5,112,306 A | 5/1992 | Burton et al. | |
| 5,250,029 A * | 10/1993 | Lin | A61M 25/0017 604/103.11 |
| 5,308,318 A * | 5/1994 | Plassche, Jr. | A61M 25/0147 604/540 |

(Continued)

FOREIGN PATENT DOCUMENTS

WO WO 2012/006629 1/2012

OTHER PUBLICATIONS

Patent Cooperation Treaty; PCT International Search Report, Issued in Connection with PCT/US2014/012808; dated Jun. 12, 2014; 7 pages; Europe.

(Continued)

*Primary Examiner* — Adam Marcetich
(74) *Attorney, Agent, or Firm* — Greenberg Traurig LLP (57) ABSTRACT

A method and apparatus for treatment of human urinary incontinence may include a flexible tube, a retainer member for the tube, and a valve in the tube which automatically opens in response to a predetermined pressure level in the bladder acting upon the valve.

9 Claims, 5 Drawing Sheets

(56) References Cited

U.S. PATENT DOCUMENTS

| | | | | |
|---|---|---|---|---|
| 5,417,657 A | * | 5/1995 | Hauer | A61M 25/0017 604/103.02 |
| 5,707,357 A | * | 1/1998 | Mikhail | A61M 25/0017 604/167.03 |
| 5,785,641 A | | 7/1998 | Davis | |
| 5,989,288 A | * | 11/1999 | Pintauro | A61F 2/0022 600/29 |
| 6,167,886 B1 | | 1/2001 | Engel et al. | |
| 7,037,303 B2 | | 5/2006 | Beaufore et al. | |
| 2003/0195456 A1 | * | 10/2003 | Robertson | A61M 27/008 604/8 |
| 2003/0199986 A1 | * | 10/2003 | McWeeney | A61F 2/0022 623/23.7 |
| 2004/0049170 A1 | | 3/2004 | Snell | |
| 2004/0097794 A1 | * | 5/2004 | Bonutti | A61B 17/0218 600/207 |
| 2005/0124978 A1 | | 6/2005 | Kim | |
| 2005/0149201 A1 | | 7/2005 | McWeeney et al. | |
| 2007/0161940 A1 | * | 7/2007 | Blanchard | A61M 5/16881 604/6.1 |
| 2007/0213661 A1 | * | 9/2007 | Gobel | A61F 2/0013 604/96.01 |
| 2008/0269546 A1 | | 10/2008 | Wilkie et al. | |
| 2009/0192451 A1 | | 7/2009 | Mroncz et al. | |
| 2009/0221992 A1 | * | 9/2009 | Hannon | A61M 25/007 604/544 |
| 2010/0114006 A1 | * | 5/2010 | Baerveldt | A61F 9/007 604/8 |
| 2010/0331608 A1 | | 12/2010 | Trubiano | |
| 2011/0160706 A1 | | 6/2011 | Behan | |
| 2011/0238042 A1 | * | 9/2011 | Davis | A61M 25/0017 604/544 |
| 2012/0108889 A1 | * | 5/2012 | Behan | A61F 2/0009 600/30 |
| 2013/0197486 A1 | | 8/2013 | Aaronson et al. | |

OTHER PUBLICATIONS

PCT/US2014/012808, Javier G. Reyes, PCT Invitation to Pay Additional Fees, Apr. 24, 2014.

* cited by examiner

METHOD AND APPARATUS FOR TREATMENT OF HUMAN URINARY INCONTINENCE

RELATED APPLICATION

This Application claims the benefit, and priority benefit, of U.S. Patent Application Ser. No. 61/756,725, filed Jan. 25, 2013, entitled "Method and Apparatus for Treatment of Human Urinary Incontinence".

BACKGROUND OF THE INVENTION

1. Field of the Disclosure

This disclosure relates generally to the field of treatment of human, male or female, urinary incontinence.

2. Description of the Related Art

Voluntary control over discharge of bladder contents, such as urine, is a serious and distressing problem for person whose natural anatomy is no longer capable of completely controlling the outflow of urine from the bladder because of the person's advanced age, surgery, disease, stroke, trauma, or other malformation of the natural lower urinary tract. Urinary incontinence is understood as meaning the involuntary loss of urine from the urinary bladder and urethra. In some cases of incontinence, the excretion of urine occurs uncontrollably and without complete emptying the volume of the bladder.

Urinary incontinence has been treated with anticholinergic medications which are used to treat incontinence and overactive bladders. Additionally, urethral balloon catheters, known as Foley catheters, have been used. Conventional Foley catheters include a flexible tube which extends from outside the body along the urethra and into the bladder. Urine is continuously drained through the flexible tube into a bag which is worn by the patient. Various types of valved urinary catheters have also been proposed, wherein various types of valves are manually opened by the incontinent person, such as by deforming and squeezing a valve to permit urine to be drained from the person's bladder.

BRIEF SUMMARY

The following presents a simplified summary of the disclosed subject matter in order to provide a basic understanding of some aspects of the subject matter disclosed herein. This summary is not an exhaustive overview of the technology disclosed herein. It is not intended to identify key or critical elements of the invention or to delineate the scope of the invention. Its sole purpose is to present some concepts in a simplified form as a prelude to the more detailed description that is discussed later.

In one illustrative embodiment, an apparatus for treatment of human urinary incontinence to be used by a human being having a bladder and a urethra is disclosed which comprises: an elongate tube having first and second ends, a longitudinal axis, and inner and outer wall surfaces, the first end adapted to be disposed adjacent the bladder of the human being and in fluid communication with the bladder for the passage of urine present in the bladder to flow into the first end of the elongate tube; a retainer member connected to the first end of the elongate tube and adapted to retain the first end of the elongate tube in fluid communication with the bladder; a valve disposed adjacent the second end of elongate tube and adapted to be disposed within the urethra, the valve including at least one slit having a longitudinal axis and the at least one slit is disposed in the elongate tube and extends between the inner and outer wall surfaces of the tube, with the longitudinal axis of the at least one slit being disposed substantially parallel with the longitudinal axis of the elongate tube; the valve having a normally first closed configuration, wherein the at least one slit is closed and urine cannot flow outwardly from the elongate tube through the valve and into the urethra, and a second open configuration wherein at least one of the at least one slits is open and urine can flow outwardly from the elongate tube through the valve and into the urethra, the valve automatically opening and having the second open configuration in response to a predetermined pressure level in the bladder acting upon the valve.

In another illustrative embodiment, an apparatus for treatment of human urinary incontinence to be used by a human being having a bladder and a urethra is disclosed which comprises: an elongate tube having first and second ends, a longitudinal axis, and inner and outer wall surfaces, the first end adapted to be disposed adjacent the bladder of the human being and in fluid communication with the bladder for the passage of urine present in the bladder to flow into the first end of the elongate tube; a retainer member connected to the first end of the elongate tube and adapted to retain the first end of the elongate tube in fluid communication with the bladder; a slit valve disposed adjacent the second end of elongate tube and adapted to be disposed within the urethra, the valve including at least one slit having a longitudinal axis, with the longitudinal axis of the at least one slit being disposed substantially perpendicular to the longitudinal axis of the elongate tube; the valve having a normally first closed configuration, wherein the at least one slit is closed and urine cannot flow outwardly from the elongate tube through the valve and into the urethra, and a second open configuration wherein at least one of the at least one slits is open and urine can flow outwardly from the elongate tube through the valve and into the urethra, the valve automatically opening and having the second open configuration in response to a predetermined pressure level in the bladder acting upon the valve.

In another illustrative embodiment, a method of treatment of human urinary incontinence in a human being having a bladder and a urethra is disclosed, comprising: providing an apparatus for treatment of human urinary incontinence, the apparatus including: an elongate tube having first and second ends, a longitudinal axis, and inner and outer wall surfaces; a retainer member connected to the first end of the elongate tube; a valve disposed adjacent the second end of elongate tube; the valve including at least one slit having a longitudinal axis and the at least one slit is disposed in the elongate tube and extends between the inner and outer wall surfaces of the tube, with the longitudinal axis of the at least one slit being disposed substantially parallel with the longitudinal axis of the elongate tube; the valve having a normally first closed configuration, wherein the at least one slit is closed and urine present in the bladder cannot flow outwardly from the elongate tube through the valve and into the urethra, and a second open configuration wherein at least one of the at least one slits is open and urine present in the bladder can flow outwardly from the elongate tube through the valve and into the urethra; disposing the first end of the elongate tube adjacent the bladder of the human being and in fluid communication with the bladder for the passage of urine present in the bladder to flow into the first end of the elongate tube; disposing the retainer member in the bladder and retaining the first end of the elongate tube in fluid communication with the bladder; disposing the second end of the elongate tube in the urethra with the valve disposed within the urethra; and automatically opening the valve to the second open configuration in response to a predetermined pressure level in the bladder acting upon the valve, whereby urine can flow outwardly from the elongate tube through the valve and into the urethra.

In another illustrative embodiment, a method of treatment of human urinary incontinence in a human being having a bladder and a urethra is disclosed, comprising: providing an apparatus for treatment of human urinary incontinence, the apparatus including: an elongate tube having first and second ends, a longitudinal axis, and inner and outer wall surfaces; a retainer member connected to the first end of the elongate tube; a valve disposed adjacent the second end of elongate tube; the valve including at least one slit having a longitudinal axis, with the longitudinal axis of the at least one slit being disposed substantially perpendicular with the longitudinal axis of the elongate tube; the valve having a normally first closed configuration, wherein the at least one slit is closed and urine present in the bladder cannot flow outwardly from the elongate tube through the valve and into the urethra, and a second open configuration wherein at least one of the at least one slits is open and urine present in the bladder can flow outwardly from the elongate tube through the valve and into the urethra; disposing the first end of the elongate tube adjacent the bladder of the human being and in fluid communication with the bladder for the passage of urine present in the bladder to flow into the first end of the elongate tube; disposing the retainer member in the bladder and retaining the first end of the elongate tube in fluid communication with the bladder; disposing the second end of the elongate tube in the urethra with the valve disposed within the urethra; and automatically opening the valve to the second open configuration in response to a predetermined pressure level in the bladder acting upon the valve, whereby urine can flow outwardly from the elongate tube through the valve and into the urethra.

BRIEF DESCRIPTION OF THE DRAWING

The present method and apparatus for treatment of human urinary incontinence may be understood by reference to the following description taken in conjunction with the accompanying drawing, in which.

While certain embodiments of the present method and apparatus for treatment of human urinary incontinence will be described in connection with the preferred illustrative embodiments shown herein, it will be understood that it is not intended to limit the invention to those embodiments. On the contrary, it is intended to cover all alternatives, modifications, and equivalents, as may be included within the spirit and scope of the invention as defined by the appended claims. In the drawing figures, which are not to scale, the same reference numerals are used throughout the description and in the drawing figures for components and elements having the same structure, and primed reference numerals are used for components and elements having a similar function and construction to those components and elements having the same unprimed reference numerals.

DETAILED DESCRIPTION OF THE SPECIFIC EMBODIMENTS

Figure 1:
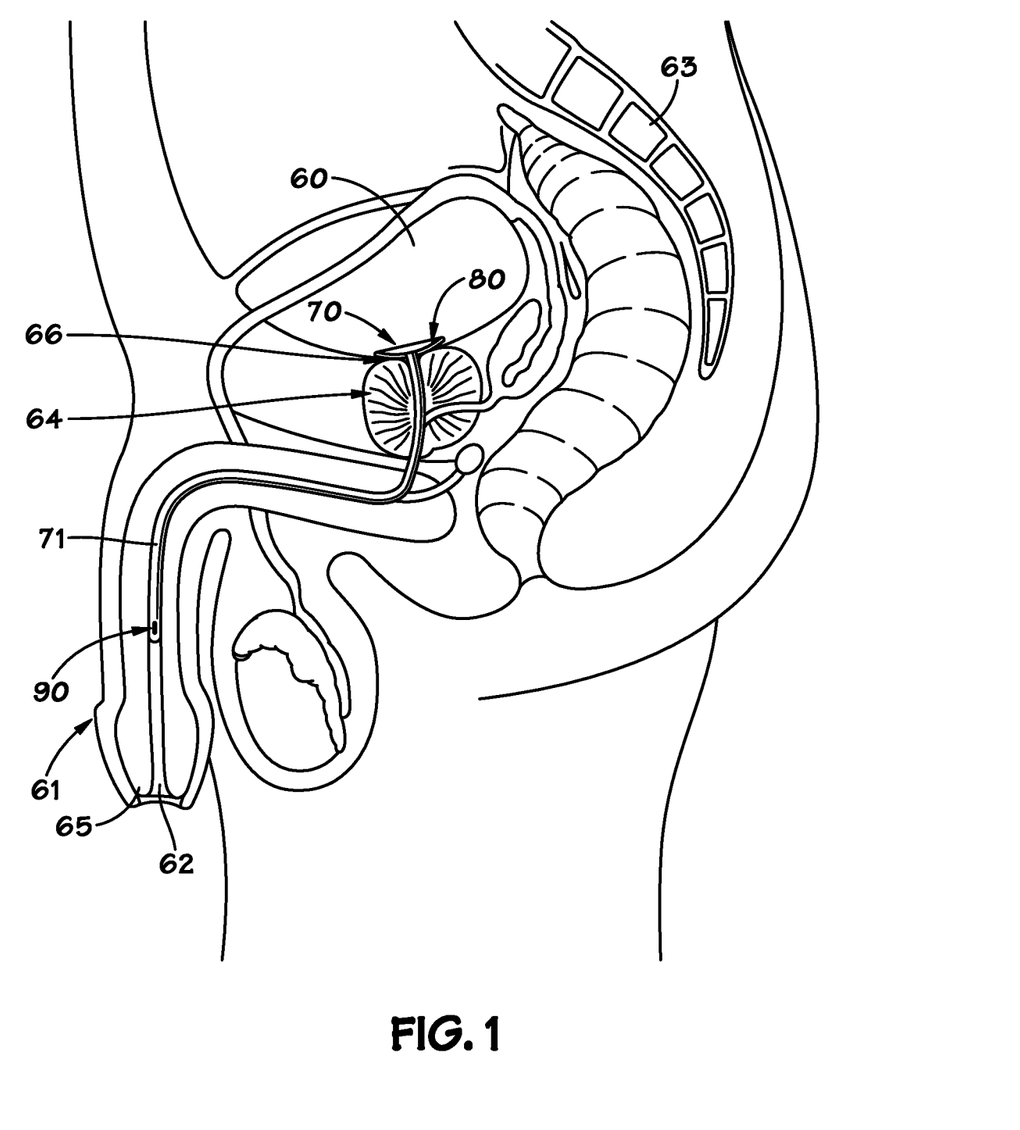
FIG. 1 is a partial cross-sectional view of a human male, including an embodiment of the present apparatus for treatment of human urinary incontinence.

With reference to FIG. 1, a portion of the human male anatomy is shown, including the urinary bladder 60, penis 61, and urethra 62. Other parts of the anatomy illustrated include the lower portion of spine 63, prostate gland 64 located below bladder 60 and surrounding a portion of the urethra 62. The urethra 62 extends from the head 65 of penis 61 to the neck 66 of bladder 60. Urine (not shown) collects in the urinary bladder 60 and in a healthy human, not suffering from urinary incontinence, the bladder is emptied and the person urinates by consciously contracting his, or her, abdominal muscles which permits urine to flow outwardly from bladder 60 into urethra 62. In this regard, a person's desire to urinate is typically dependant upon fluid, or urine, pressure within the bladder 60, or the vesical pressure, rather than the volume of fluid, or urine, contained in bladder 60. As will be hereinafter described in greater detail, an embodiment of the present apparatus 70 for treatment of human urinary incontinence is shown disposed within bladder 60 and urethra 62.

Figure 2:
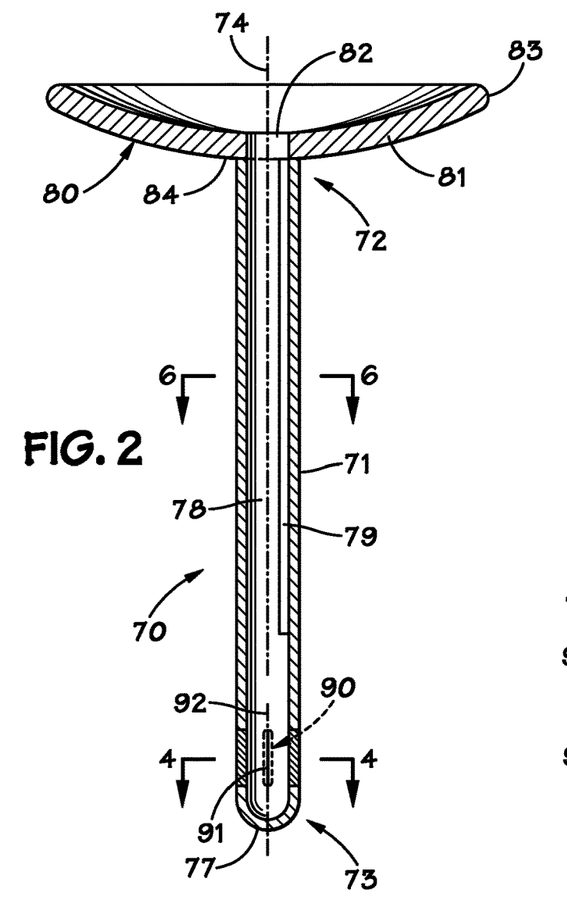
FIG. 2 is a front, partial cross-sectional view of the apparatus of FIG. 1.
Figure 3:
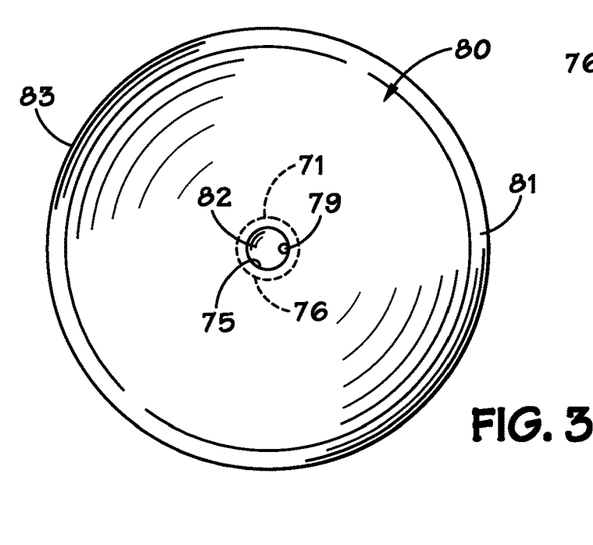
FIG. 3 is a top view of the apparatus of FIG. 2.
Figure 4:
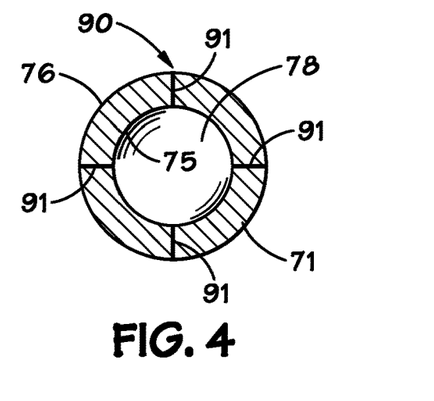
FIG. 4 is a cross-sectional view taken along line 4-4 of FIG. 2.
Figure 5:
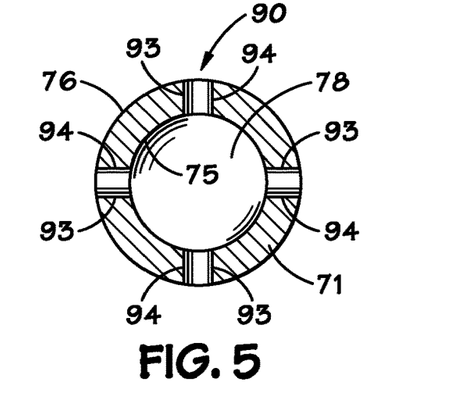
FIG. 5 is a cross-sectional view of the apparatus of FIG. 2 when the valve is open, and is similar to the view of FIG. 4.
Figure 6:
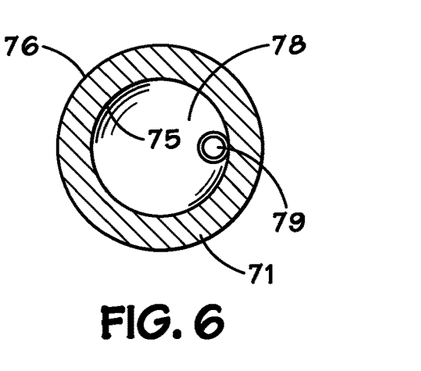
FIG. 6 is a cross-sectional view of the apparatus of FIG. 2 taken along line 6-6 of FIG. 2.

With reference to FIGS. 2-5, the present apparatus 70 for treatment of urinary incontinence generally includes: an elongate tube 71, a retainer member 80, and a valve 90. Elongate tube 71 has first and second ends 72, 73, a longitudinal axis 74, and inner and outer wall surfaces 75, 76. As seen in FIGS. 4 and 5, elongate tube 71 has a generally circular cross-sectional configuration forming a lumen 78, although other cross-sectional configurations could be utilized, such as an oval shaped cross-sectional configuration. As seen in FIG. 2, the second end 73 of elongate tube 71 is preferably closed, or sealed, by a generally spherical tip portion 77. If desired, the second end 73 of elongate tube 71 could be sealed by other tip portions having configuration other than spherical, such as a flat tip surface (not shown) disposed substantially perpendicular to the longitudinal axis 74 of elongate tube 71. Preferably, as will be hereinafter described in greater detail, elongate tube 71 is of a flexible construction, and preferably made of a flexible material.

Retainer member 80 is connected, or associated with, the first end 72 of elongate tube 71. Preferably, retainer member 80 is connected, or associated with, the first end 72 of elongate tube 71 as by forming retainer member and tube 71 integral with each other as by molding retainer member 80 and elongate tube 71 together in a single mold. Alternatively, retainer member may be connected to tube 71 in any suitable manner, such as by suitable biologically compatible adhesive or epoxy, or by heat sealing retainer member 80 to tube 71. As seen in FIGS. 2 and 3, retainer member 80 may include a disc-shaped member 81 having a generally circular configuration as shown in FIG. 3. Alternatively, retainer member 80 may have other shapes other than the disc-shaped configuration of member 81, such as an oval, square, rectangular, or any other desired configuration.

Retainer member 80 also includes an opening 82 formed in the disc-shaped member 81. Preferably as shown in FIG. 3, the opening 82 is disposed substantially in the center of disc-shaped member 81; however, opening 82 could be formed at other locations of disc-shaped member 81, provided the opening 82 is in fluid communication, or in a mating relationship, with the first end 72 of elongate tube 71. Preferably opening 82 has a generally circular shaped configuration; however, opening 82 could have other configurations other than circular, such as an oval shape, square shape, or any other desired shape or configuration. The general construction of retainer member 80 may be a flexible construction, is by forming retainer member 80 of a flexible material, as will be hereinafter described in greater detail. If desired, retainer member 80 may have an inflatable construction. Disc-shaped member 81 may be made of at least 2 layers (not shown) which provide an interior space, or volume, which may receive a suitable biologically compatible fluid, such as a sterile saline solution, to inflate the disc-shaped member 81. In this regard, retainer member 80 which is seen to have a generally concave configuration, wherein the outer circumference 83 of disc-shaped member 81 is disposed slightly higher than the lower-most portion 84 of disc-shaped member 81 where opening 82 is located. Disc-shaped member 81 may be formed, as by molding, to have the generally concave configuration shown in FIGS. 2 and 3. Alternatively, retainer member 80 may assume the generally slightly concave configuration shown in FIGS. 2 and 3, upon inflating retainer member 80. Alternatively, retainer member 80 may be formed as a substantially flat, planar, disc-shaped member 81 which lies in a plane which is substantially perpendicular to the longitudinal axis 74 of tube 71.

Still with reference to FIGS. 2-5, valve 90 is disposed adjacent the second end 73 of the elongate tube 71, and valve 90 preferably includes, at least one slit 91. Slit 91 has a longitudinal axis 92 and the longitudinal axis 92 is substantially parallel with the longitudinal axis 74 of tube 71. Slit 91 extends between the inner and outer wall surfaces 75, 76 of tube 91. In the embodiment of the present apparatus 70 illustrated in FIGS. 2-5, four slits 91 are illustrated, although a larger number, or lesser number, of slits 91 could be provided, such as two or five, etc. As shown in FIGS. 4 and 5, slits 91 are preferably equidistantly disposed about the circumference of outer wall surface 76 of tube 71. As shown in FIG. 4, each slit 91 is preferably disposed substantially perpendicular to the inner and outer wall surfaces 75, 76 of tube 71. At least one slit 91 may be provided in tube 71, as by molding slit 91 into tube 71, or alternatively by cutting slit 91 in tube 71 with a sharp knife or razor or similar cutting tool, after tube 71 has been formed as by molding or casting.

Valve 90, as seen in FIG. 4 has a normally first closed configuration, wherein the two opposed wall surfaces 93, 94 (FIG. 5) of slit 91 are in an abutting, or closed, configuration, wherein urine cannot flow outwardly from the elongate tube 71 through valve 90, as will be hereinafter described in greater detail. Valve 90 has a second open configuration, as illustrated in FIG. 5, wherein the at least one slit 91 is open, and the opposed wall surfaces 93, 94 of slit 91, are spaced apart from each other, and urine can flow outwardly from the elongate tube 71, as will be hereinafter described in greater detail. Valve 90 automatically opens and has the second open configuration shown in FIG. 5, upon a predetermined pressure level in the bladder 60 (FIG. 1) acting upon the valve 90, as will be hereinafter described in greater detail.

Preferably, apparatus 70, including elongate tube 71 and retainer member 80, are formed of a suitable biologically compatible material, which may be an elastomeric material. Preferably the elastomeric material is silicone, such as any number of suitable medical grade silicones. Retainer member 80 and elongate tube 71 may be treated, coated, or impregnated, with at least one antibiotic to prevent bacterial colonization and the decrease of build up of mucoid film that will increase the durability and patency of apparatus 70. Preferably the entire apparatus 70, retainer member 80 and tube 71, are treated, coated, or impregnated, with the at least one antibiotic. Alternatively, the retainer member 80 and elongate tube 71 could also be treated, coated, or impregnated with silver to release silver ions into the urethra 62 and bladder 60 to reduce mucoid film or biofilm formation and bacteria colonization to reduce the risk of infection.

As to the predetermined pressure level in the bladder 60 which in turns acts upon valve 90, the predetermined pressure level at which valve 90 opens is selected by the physician implanting apparatus 70 based upon various factors, such as the age, general health, and mental abilities of the person to be treated with apparatus 70, as to how often valve 90 is to automatically open. For example, a potential predetermined pressure level may be described as a high pressure level of approximately 11 to 18 cm. H20, wherein the person's bladder pressure level must reach that pressure level, or high pressure level, before valve 90 will automatically open. A valve 90 opening at such a high pressure level may be suitable for a person of diminished mental capacity, such as an elderly nursing home patient having dementia, whereby a great deal of pressure or force, is necessary before valve 90 opens. Pressure could be allowed to build up, whereby a person could be taken by a nurses aide after a long interval of time to ask the person to urinate into a toilet by contracting his or her abdominal muscles, or straining, as they did in the past when the person wanted to urinate. Another pressure level, or medium pressure level, could be approximately 5 to 9 cm. H20 and a low pressure level could be 2 to 5 cm H20. A valve 90 opening at the lower pressure level may be suitable for a person of good general health, whereby that person would routinely go on a schedule of shorter intervals to a restroom to urinate by contracting his or her abdominal muscles to urination. The apparatus 70 could be manufactured to have the desired pressure level which opens valve 90, as by varying the size, or the length, of the at least one slit 91, as well as by varying the wall thickness of tube 71 where slit 91 is provided.

Apparatus 70 may have the same construction for both males and females, with the exception that the length of elongate tube 71 would differ depending upon if apparatus 70 is intended to be used for a male or female. For a male, the length of elongate tube 71 may be approximately 5 to 6 inches and for a female the length of tube 71 would be approximately 2 to 2½ inches in length. As will be hereinafter described in greater detail, the length of tube 71 for a male is selected, so that the second end 73 of tube 71, when implanted in a male, is disposed in urethra 62 in a spaced relationship from penis head 65 as shown in FIG. 1.

With reference to FIGS. 1 4, and 5, the present method of treatment of human urinary incontinence in a human will be described. The apparatus 70, previously described is disposed in a person with the first end 72 of tube 71 disposed adjacent the bladder 60, with the first end 72 of tube 71 in fluid communication with bladder 60 so that urine present in bladder 60 may flow into the first end 72 of tube 71. Retainer member 80 which is connected to the first end 72 of tube 71, as previously described and as shown in FIG. 1, is disposed in bladder 60. Retainer member 80 retains the first end 72 of tube 71 in fluid communication with bladder 60, and opening 82 (FIG. 3) is in fluid communication with the lumen 78 of tube 71.

As seen in FIG. 1, valve 90 of apparatus 70 is disposed within urethra 62 in a spaced relationship from the penis head 65, whereby the elongate tube 71 does not extend outwardly from the urethra 62. Simarily, when apparatus 70 is utilized by a female, second end 73 of tube 71 would not extend outside a female's urethra 62, but would also be spaced apart from the end of the female's urethra.

Figure 7:
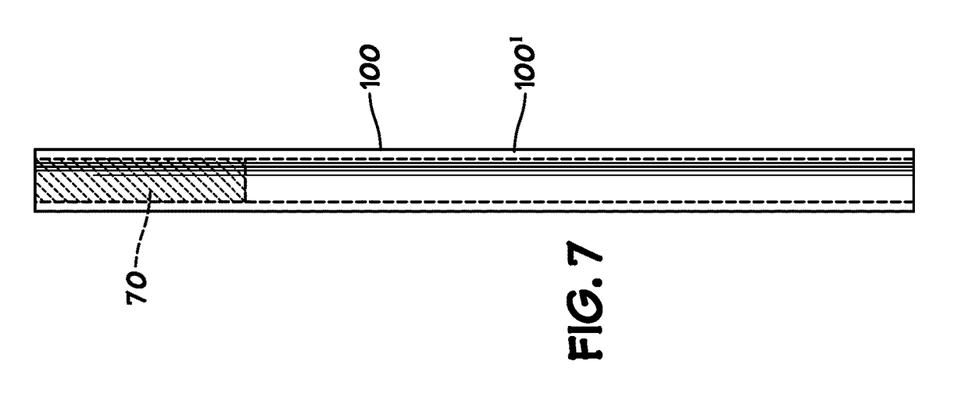
FIG. 7 is a schematic, partial cross-sectional view of a delivery catheter or cystoscope for use with the apparatus of FIG. 2 and FIGS. 8-10.

With reference to FIGS. 1 and 4-7, the present method of treatment of urinary incontinence generally includes apparatus 70 as previously described, disposed in fluid communication with bladder 60. Apparatus 70 is collapsed and placed within a delivery catheter 100 (FIG. 7), and the delivery catheter 100, in a conventional manner, is passed through the person's urethra 62 until the retainer member 80 is disposed within bladder 60 as shown in FIG. 1. Upon removal or withdrawal of the delivery catheter 100 in a conventional manner, retainer member 80 remains within bladder 60, and tube 71 is left disposed within urethra 62, as shown is FIG. 1. Alternatively, apparatus 70 could be delivered, or inserted, within the bladder 60 and urethra 62 by use of a conventional cystoscope 100' (FIG. 7).

As tube 71 is of flexible construction, as previously described, tube 71 conforms to the curving configuration of urethra 62. Disc-shaped member 81 of retainer member 80 is disposed in a sealing relationship with at least a portion of the bladder 60, as by lying upon and over the neck 66 of bladder 60. If disc-shaped member 81 is of a flexible construction, disc-shaped member 81 lays over neck 66 of bladder 60. Retainer member 80 retains the first end 72 of elongate tube 71 in fluid communication with bladder 60, as by opening 82 (FIG. 3) of disc-shaped member 81 being in fluid communication with the lumen 78 of tube 71. Delivery catheter 100 may be of any suitable conventional construction as are known in the art.

If retainer member 80 is provided with an inflatable disc-shaped member 81, as previously described, the inflatable retainer member 80 may be inflated by passing a biologically compatible fluid, such as a sterile saline solution, through a fluid passageway having a lumen 79 (FIGS. 2 and 6) associated with tube 71, which fluid may then inflate retainer member 80 to maintain it in a sealing relationship with the neck 66 of bladder 60. In an apparatus 70 for use with males, the fluid passageway and lumen 79 may have a length of approximately from 3½ to 4 inches; and for females the length of the fluid passageway and lumen 79 may be approximately 1½ to 2 inches. The fluid could be injected into, or disposed, within lumen 79 in any conventional manner.

In use, a person having apparatus 70 implanted may go about his or her normal activities during which time valve 90 remains in its normally first closed configuration as illustrated and described in connection with FIG. 4. For a person having sufficient mental capabilities desires to urinate, that person would contract his or her abdominal muscles to increase the vesical pressure, or bladder fluid pressure, to exceed the predetermined pressure level at which valve 90 opens and assumes it second open configuration, as previously shown and described in connection with FIG. 5. Upon the predetermined pressure level in the person's bladder being lowered due to urination, valve 90 assumes it normally first closed configuration as shown in FIG. 4 and the person may then again pursue his or her normal activities. As previously described in connection with a person with more limited mental and/or physical capabilities, that person would be taken on a schedule to a toilet and the person would not have had his or her bladder pressure level exceed that pressure level which would open valve 90. At that time, the person would be encouraged to urinate by contracting his or her abdominal muscles to increase the bladder pressure beyond the predetermined pressure level at which valve 90 opens and automatically assumes the second open configuration shown in FIG. 5.

It is believed that the apparatus 70 may remain within a person, as shown in FIG. 1, for approximately 4 to 6 months, after which time the apparatus 70 could be removed in a conventional manner for removal of a catheter and withdrawn from the person's bladder and urethra. If an inflatable retainer member 80 is utilized, the sterile saline solution may be removed in a conventional manner through the fluid passageway and lumen 79, prior to removing apparatus 70 from the person's bladder 60 and urethra 62, such as by use of a bayonet forceps (not shown). After the removal of the apparatus 70, another apparatus 70 could be implanted and delivered as previously described.

Figure 8:
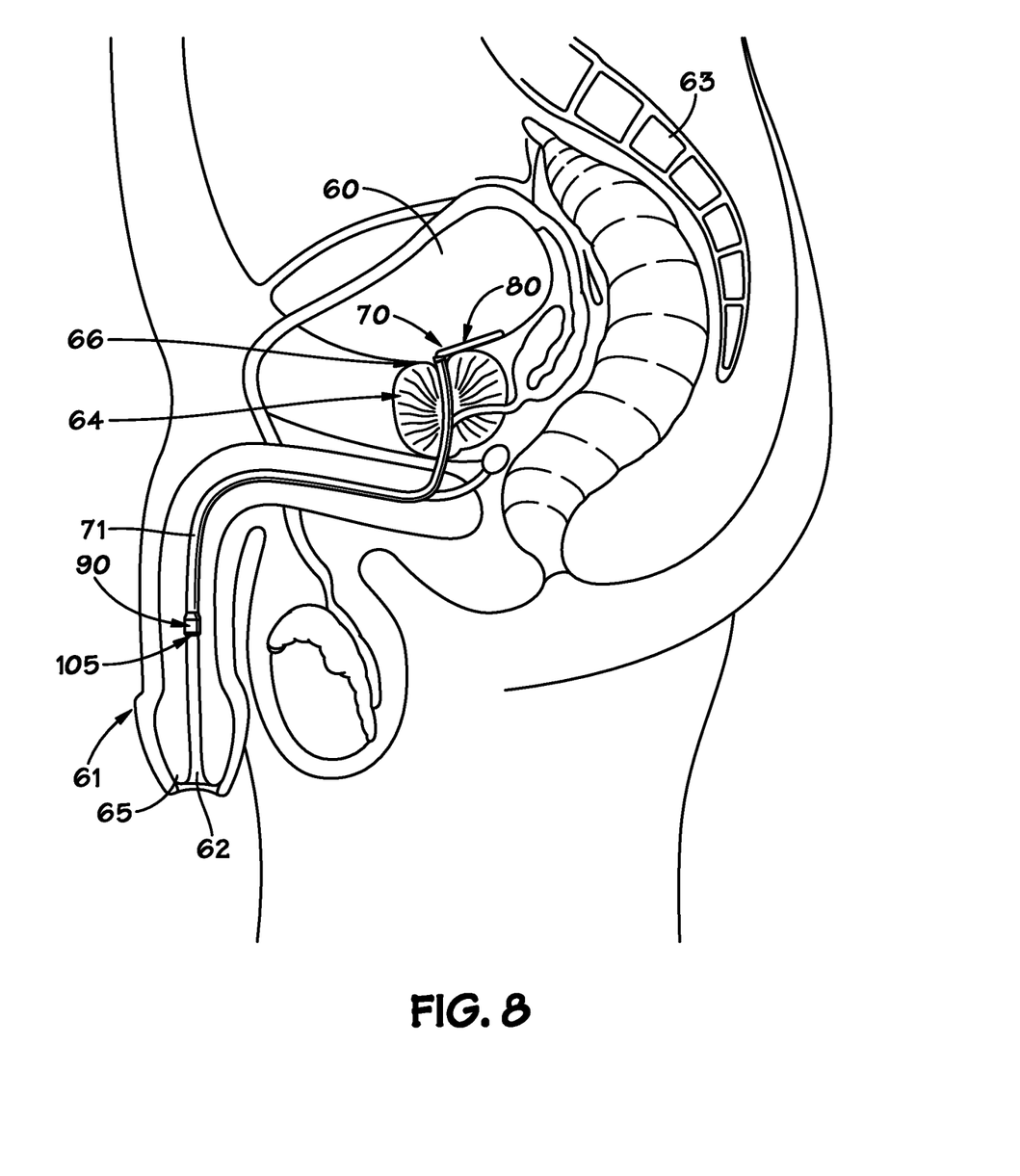
FIG. 8 is a partial cross-sectional view of a human male, including another embodiment of the present apparatus for treatment of human urinary incontinence.

With reference to FIG. 8, a portion of the human male anatomy is shown, as previously described in connection with FIG. 1. As will be hereinafter described in greater detail, another embodiment of the present apparatus 70' for treatment of human urinary incontinence is shown disposed within bladder 60 and urethra 62.

Figure 9:
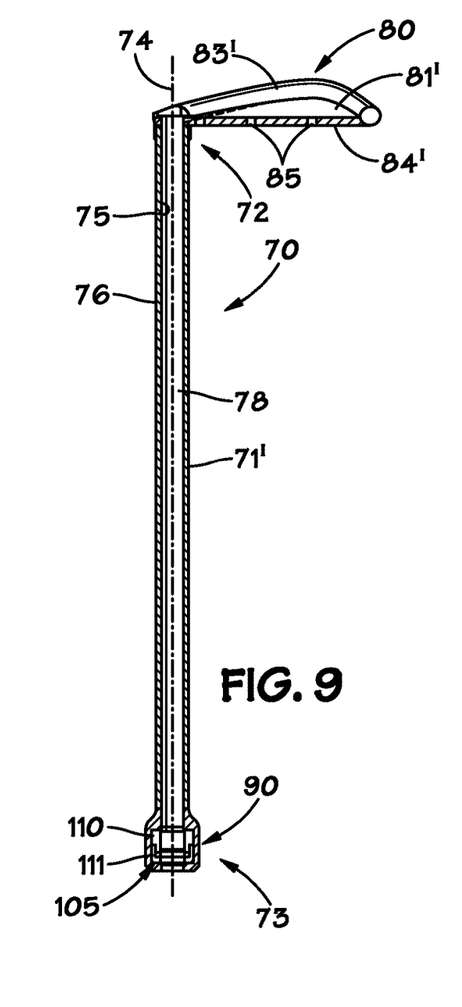
FIG. 9 is a front, partial cross-sectional view of the apparatus of FIG. 8.
Figure 10:
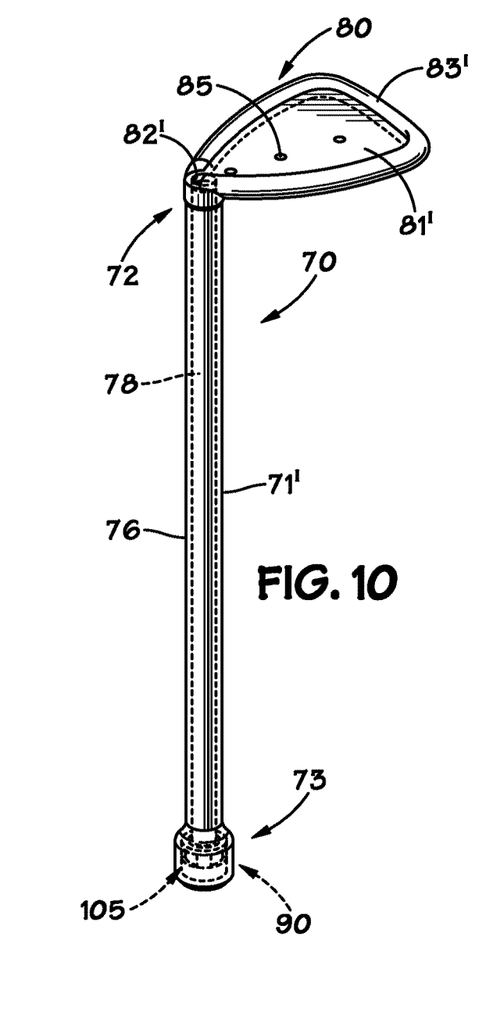
FIG. 10 is a perspective view of the apparatus of FIGS. 8 and 9.

With reference to FIGS. 8-11, this embodiment of the present apparatus 70' for treatment of urinary incontinence generally includes: an elongate tube 71', a retainer member 80, and a valve 90. Elongate tube 71' has first and second ends 72, 73, a longitudinal axis 74, and inner and outer wall surfaces 75, 76. Elongate tube 71' has a generally circular cross-sectional configuration forming a lumen 78, although other cross-sectional configurations could be utilized, such as an oval shaped cross-sectional configuration. As seen in FIGS. 9 and 10, the second end 73 of elongate tube 71' is preferably closed, or sealed, by a generally, circular-shaped valve housing 105. If desired, the second end 73 of elongate tube 71' could be sealed by other valve housings having configurations other than circular, such as oval, or similar rounded shapes. Preferably, as will be hereinafter described in greater detail, elongate tube 71' is of a flexible construction, and preferably made of a flexible material.

Figure 11:
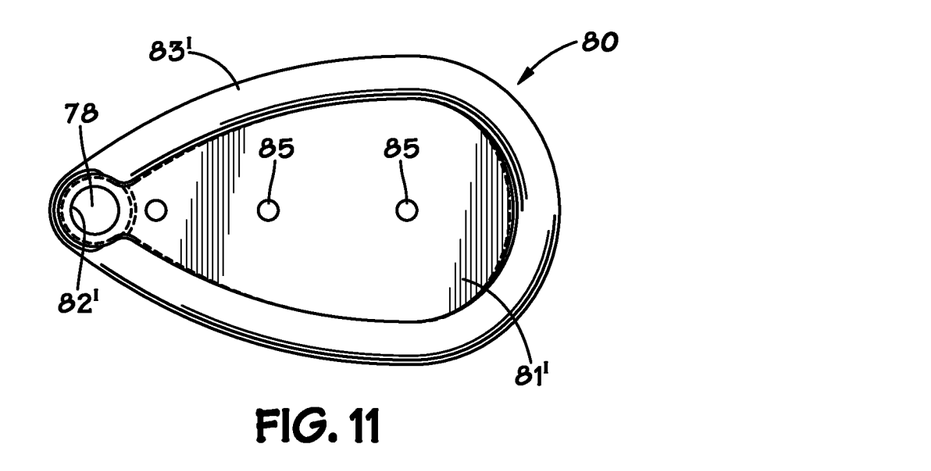
FIG. 11 is a top view of a retainer member of the apparatus of FIGS. 8 and 9.

Retainer member 80 is connected, or associated with, the first end 72 of elongate tube 71'. Retainer member 80 is connected, or associated with, the first end 72 of elongate tube 71' as by forming retainer member and tube 71' integral with each other as by molding retainer member 80 and elongate tube 71' together in a single mold. Alternatively, retainer member may be formed independent from tube 71' and may be connected to tube 71' in any suitable manner, such as by suitable biologically compatible adhesive or epoxy, or by heat sealing retainer member 80 to tube 71'. As seen in FIGS. 9-11, retainer, or anchor, member 80 may include a generally concave, disc-shaped member 81' having a generally rounded, tear drop configuration as shown in FIG. 11. Alternatively, retainer member 80 may have other shapes other than the generally concave, rounded tear drop configuration of FIGS. 9-11, such as an oval, square, rectangular, or any other desired configuration. By the use of the term "tear drop" is meant something, when viewed from above as in FIG. 11, that is shaped like a drop of liquid having a globular form at one end and tapering to a rounded point at the other end, or is shaped like a falling tear like a gem, as on an earring, necklace, or ring. By the use of the term "concave" is meant something that is hollowed or rounded inward like the inside of a bowl. Retainer member 81' with its generally rounded, concave, tear drop configuration readily conforms to the interior surface of bladder 60, FIG. 1.

Retainer member 80 also includes an opening 82' formed in the disc-shaped member 81'. Preferably as shown in FIG. 11, the opening 82' is disposed substantially at the apex, or rounded, narrowed end of disc-shaped member 81; however, opening 82' could be formed at other locations of disc-shaped member 81', provided the opening 82' is in fluid communication, or in a mating relationship, with the first end 72 of elongate tube 71'. Preferably opening 82' has a generally circular shaped configuration; however, opening 82' could have other configurations other than circular, such as an oval shape, square shape, or any other desired shape or configuration. The general construction of retainer member 80 may be a flexible construction, is by forming retainer member 80 of a flexible material, as will be hereinafter described in greater detail. Retainer member 80 with its generally concave configuration, has the outer surface 83' of disc-shaped member 81' disposed slightly higher than the lower-most portion 84' of disc-shaped member 81'. Disc-shaped member 81' may be formed, as by molding, to have the generally concave configuration shown in FIGS. 8-11. Alternatively, retainer member 80 may be formed as a substantially flat, planar, disc-shaped member 81' which lies in a plane which is substantially perpendicular to the longitudinal axis 74 of tube 71. The outer surface 83' of disc-shaped member 81' may have a generally circular configuration as shown in FIGS. 9 and 10, but other generally rounded, smooth, configurations could be utilized. If desired, one or more drain openings may be formed in member 81'.

With reference to FIGS. 9, 10, 12, and 13, valve 90 is disposed adjacent the second end 73 of the elongate tube 71, within valve housing 105. Valve 90 preferably includes, at least one slit 91'. Slits 91' have a longitudinal axis 92' and the longitudinal axes 92' lie in a plane which is substantially perpendicular to the longitudinal axis 74 of tube 71'. In the present embodiment of the apparatus 70 illustrated in FIGS. 8-13, two slits 91' are illustrated, although a larger number, or lesser number, of slits 91' could be provided, such as three, four or five, etc. At least one slit 91' may be provided in valve 90, as by molding slit 91' into valve 90, or alternatively by cutting slit 91' in valve 90 with a sharp knife or razor or similar cutting tool. Valve, or cruciform shaped slit valve, 90 has a substantially circular outer configuration, which is received within valve housing 105, as shown in FIGS. 9 and 10, although other outer configurations could be utilized, if desired, provided they cooperate with valve housing 105.

Figure 12:
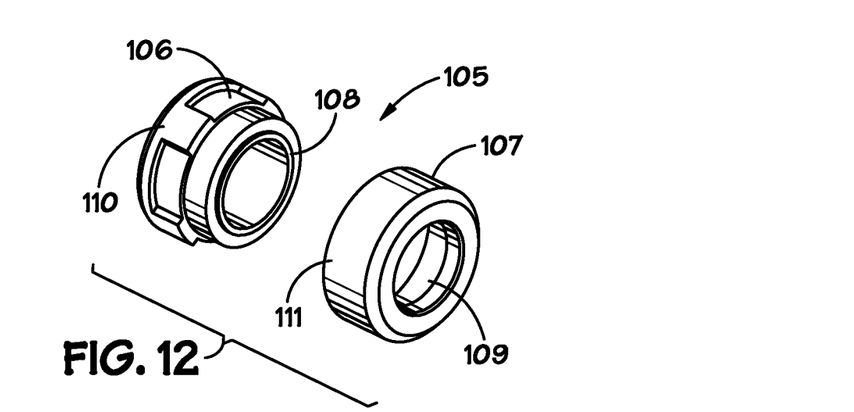
FIG. 12 is an exploded view of a valve housing of the apparatus of FIGS. 8-10.

Valve housing 105 preferably is formed of two valve housing members 106 and 107, between which valve 90 is retained in a sealing relationship. Housing member 106 may have a male, annular flange 108, which is received within a female, annular recess 109 in housing member 107. Housing members 106 and 107 may be secured to each other, with valve 90 disposed therebetween by any suitable connection such as a threaded connection formed on flange 108 and recess 109, or by gluing, heat sealing, or welding, housing members 106 and 107 together, or by use of any other suitable technique. Preferably housing members 106 and 107 are formed of a suitable medical grade, plastic material having the requisite strength and rigidity characteristics to permit it to house valve 90, and prevent the accidental opening of valve 90 by pinch forces exerted by the urethra 62 (FIG. 8), as well as being biocompatible or biologically compatible, with the patient's urethra. Although the outer wall surfaces 100, 111 of housing 105 extend outwardly beyond the outer wall surface 76 of elongate tube 71', they may be disposed co-planar with the outer wall surface 76 of tube 71', and have the same outer diameter of tube 71' if desired.

Valve 90, as seen in FIG. 8 has a normally first closed configuration, wherein the two opposed slits 91' are in an abutting, or closed, configuration, wherein urine cannot flow outwardly from the elongate tube 71' through valve 90, as will be hereinafter described in greater detail. Valve 90 has a second open configuration, wherein the at least one slit 91' is open, and the opposed wall surfaces of slit 91', are spaced apart from each other, and urine can flow outwardly from the elongate tube 71', as will be hereinafter described in greater detail. Valve 90 automatically opens and has the second open configuration upon a predetermined pressure level in the bladder 60 (FIG. 1) acting upon the valve 90, as will be hereinafter described in greater detail.

Preferably, apparatus 70, including elongate tube 71' and retainer member 80, are formed of a suitable biologically compatible material, which may be an elastomeric material. Preferably the elastomeric material is silicone, such as any number of suitable medical grade silicones. Retainer member 80 and elongate tube 71' may be treated, coated, or impregnated, with at least one antibiotic to prevent bacterial colonization and the decrease of build up of mucoid film that will increase the durability and patency of apparatus 70. Preferably the entire apparatus 70, retainer member 80 and tube 71', are treated, coated, or impregnated, with the at least one antibiotic. Alternatively, the retainer member 80 and elongate tube 71 could also be treated, coated, or impregnated with silver to release silver ions into the urethra 62 and bladder 60 to reduce mucoid film or biofilm formation and bacteria colonization to reduce the risk of infection.

As to the predetermined pressure level in the bladder 60 which in turns acts upon valve 90, the predetermined pressure level at which valve 90 opens is selected by the physician implanting apparatus 70 based upon various factors, such as the age, general health, and mental abilities of the person to be treated with apparatus 70, as to how often valve 90 is to automatically open. For example, a potential predetermined pressure level may be described as a high pressure level of approximately 11 to 18 cm. H20, wherein the person's bladder pressure level must reach that pressure level, or high pressure level, before valve 90 will automatically open. A valve 90 opening at such a high pressure level may be suitable for a person of diminished mental capacity, such as an elderly nursing home patient having dementia, whereby a great deal of pressure or force, is necessary before valve 90 opens. Pressure could be allowed to build up, whereby a person could be taken by a nurses aide after a long interval of time to ask the person to urinate into a toilet by contracting his or her abdominal muscles, or straining, as they did in the past when the person wanted to urinate.

Another pressure level, or medium pressure level, could be approximately 5 to 9 cm. H20 and a low pressure level could be 2 to 5 cm H20. A valve 90 opening at the lower pressure level may be suitable for a person of good general health, whereby that person would routinely go on a schedule of shorter intervals to a restroom to urinate by contracting his or her abdominal muscles to urination. The apparatus 70 could be manufactured to have the desired pressure level which opens valve 90, as by varying the size, or the length, of the at least one slit 91', as well as by varying the thickness of valve 90 where slit 91' is provided.

Apparatus 70 may have the same construction for both males and females, with the exception that the length of elongate tube 71' would differ depending upon if apparatus 70 is intended to be used for a male or female. For a male, the length of elongate tube 71' may be approximately 5 to 6 inches and for a female the length of tube 71' would be approximately 2 to 2½ inches in length. As will be hereinafter described in greater detail, the length of tube 71' for a male is selected, so that the second end 73 of tube 71', when implanted in a male, is disposed in urethra 62 in a spaced relationship from penis head 65 as shown in FIG. 8.

With reference to FIG. 8, the present method of treatment of human urinary incontinence in a human will be described. The apparatus 70, previously described is disposed in a person with the first end 72 of tube 71' disposed adjacent the bladder 60, with the first end 72 of tube 71' in fluid communication with bladder 60 so that urine present in bladder 60 may flow into the first end 72 of tube 71'. Retainer member 80, which is connected to the first end 72 of tube 71', as previously described and as shown in FIGS. 9-11, is disposed in bladder 60. Retainer member 80 retains the first end 72 of tube 71' in fluid communication with bladder 60, and opening 82' (FIGS. 9 and 11) is in fluid communication with the lumen 78 of tube 71'.

As seen in FIG. 8, valve 90 of apparatus 70 is disposed within urethra 62 in a spaced relationship from the penis head 65, whereby the elongate tube 71' does not extend outwardly from the urethra 62. Similarly, when apparatus 70 is utilized by a female, second end 73 of tube 71' would not extend outside a female's urethra 62, but would also be spaced apart from the end of the female's urethra.

With reference to FIGS. 7-13, the present method of treatment of urinary incontinence generally includes apparatus 70 of FIGS. 8 and 9-13 as previously described, disposed in fluid communication with bladder 60. Apparatus 70 is collapsed and placed within a delivery catheter 100 (FIG. 7), and the delivery catheter 100, in a conventional manner, is passed through the person's urethra 62 until the retainer member 80 is disposed within bladder 60 as shown in FIG. 8. Upon removal or withdrawal of the delivery catheter 100 in a conventional manner, retainer member 80 remains within bladder 60, and tube 71' is left disposed within urethra 62, as shown is FIG. 8. Alternatively, apparatus 70 could be delivered, or inserted, within the bladder 60 and urethra 62 by use of a conventional cystoscope 100' (FIG. 7).

As tube 71' is of flexible construction, as previously described, tube 71' conforms to the curving configuration of urethra 62. Disc-shaped member 81' of retainer member 80 is disposed in a sealing relationship with at least a portion of the bladder 60, as by lying upon and over the neck 66 of bladder 60. If disc-shaped member 81' is of a flexible construction, a portion of disc-shaped member 81 lays over neck 66 of bladder 60. Retainer member 80 retains the first end 72 of elongate tube 71' in fluid communication with bladder 60, as by opening 82' (FIG. 11) of disc-shaped member 81' being in fluid communication with the lumen 78 of tube 71'. Delivery catheter 100 may be of any suitable conventional construction as are known in the art.

Figure 13:
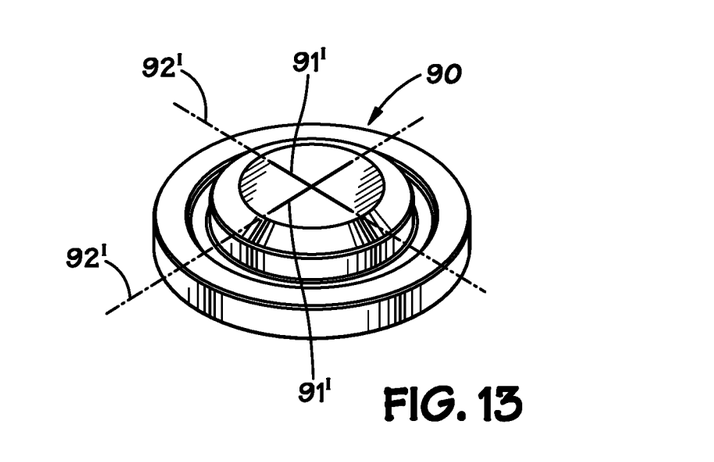
FIG. 13 is a perspective view of a valve of the apparatus of FIGS. 8-10 when the valve is closed.

In use, a person having apparatus 70 of FIGS. 8-13 implanted may go about his or her normal activities during which time valve 90 remains in its normally first closed configuration as illustrated and described in connection with FIG. 13. For a person having sufficient mental capabilities desires to urinate, that person would contract his or her abdominal muscles to increase the vesical pressure, or bladder fluid pressure, to exceed the predetermined pressure level at which valve 90 opens and assumes it second open configuration, as previously described. Upon the predetermined pressure level in the person's bladder being lowered due to urination, valve 90 assumes it normally first closed configuration as shown in FIG. 13 and the person may then again pursue his or her normal activities. As previously described in connection with a person with more limited mental and/or physical capabilities, that person would be taken on a schedule to a toilet and the person would not have had his or her bladder pressure level exceed that pressure level which would open valve 90. At that time, the person would be encouraged to urinate by contracting his or her abdominal muscles to increase the bladder pressure beyond the predetermined pressure level at which valve 90 opens.

It is believed that the apparatus 70 may remain within a person, as shown in FIG. 8, for approximately 4 to 6 months, after which time the apparatus 70 could be removed in a conventional manner for removal of a catheter and withdrawn from the person's bladder and urethra. After the removal of the apparatus 70, another apparatus 70 could be implanted and delivered as previously described.

Specific embodiments of the present method and apparatus have been described and illustrated. It will be understood to those skilled in the art that changes and modifications may be made without departing from the spirit and scope of the inventions defined by the appended claims.

I claim:

1. An apparatus for treatment of human urinary incontinence to be used by a human being having a bladder and a urethra, comprising an elongate tube having first and second ends, a longitudinal axis, and inner and outer wall surfaces, the first end adapted to be disposed adjacent the bladder of the human being and in fluid communication with the bladder for the passage of urine present in the bladder to flow into the first end of the elongate tube;

a retainer member connected to the first end of the elongate tube and adapted to retain the first end of the elongate tube in fluid communication with the bladder, wherein the retainer member is adapted to be disposed in the bladder, and includes a disc-shaped member with an opening formed in the disc-shaped member in fluid communication with the first end of the elongate tube, and wherein the disc-shaped member has a rounded, tear drop shaped configuration and a reinforced rim that is thicker than a lower most portion of the disc shaped member, and wherein the reinforced rim abuts the opening and extends around the circumference of the disc shaped member;

a valve and valve housing disposed adjacent the second end of the elongate tube and configured to be disposed within the urethra, the valve including at least one slit having a longitudinal axis and the longitudinal axis of the at least one slit is disposed substantially perpendicular to the longitudinal axis of the elongate tube; and the valve having a first closed configuration, wherein the at least one slit is closed and urine cannot flow outwardly from the elongate tube through the valve and into the urethra, and a second open configuration wherein at least one of the at least one slits is open and urine can flow outwardly from the elongate tube through the valve and into the urethra, the valve automatically opening and having the second open configuration upon a predetermined pressure level in the bladder acting upon the valve.

2. The apparatus of claim 1, wherein the disc-shaped member is flexible whereby at least a portion of the disc-shaped member is configured to lie upon at least a portion of the bladder in a sealing relationship.

3. The apparatus of claim 1, wherein the elongate tube and retainer member are formed of an elastomeric material.

4. The apparatus of claim 3, wherein the elastomeric material is silicone.

5. The apparatus of claim 1, wherein the elongate tube is treated with at least one antibiotic.

6. The apparatus of claim 1, wherein the retainer member is treated with at least one antibiotic.

7. The apparatus of claim 1, including a delivery catheter adapted for passing the elongate tube and retainer member through the urethra and disposing the retainer member in the bladder.

8. The apparatus of claim 1, wherein the valve is a cruciform shaped slit valve.

9. The apparatus of claim 1, wherein the entire circumference of the opening is enclosed within the circumference of the disc shaped member.

\* \* \* \* \*